(12) United States Patent
Llombart Juan et al.

(10) Patent No.: US 8,780,012 B2
(45) Date of Patent: Jul. 15, 2014

(54) DIELECTRIC COVERED PLANAR ANTENNAS

(75) Inventors: Nuria Llombart Juan, Alboraya (ES);
Choonsup Lee, Torrance, CA (US);
Goutam Chattopadhyay, Pasadena, CA (US); John J. Gill, La Crescenta, CA (US); Anders J. Skalare, Pasadena, CA (US); Peter H. Siegel, La Canada, CA (US)

(73) Assignee: California Institute of Technology, Pasadena, CA (US)

( * ) Notice: Subject to any disclaimer, the term of this patent is extended or adjusted under 35 U.S.C. 154(b) by 701 days.

(21) Appl. No.: 12/828,068

(22) Filed: Jun. 30, 2010

(65) Prior Publication Data
US 2010/0328779 A1 Dec. 30, 2010

Related U.S. Application Data

(60) Provisional application No. 61/221,695, filed on Jun. 30, 2009.

(51) Int. Cl.
*H01Q 19/06* (2006.01)

(52) U.S. Cl.
USPC .................................. 343/911 R

(58) Field of Classification Search
CPC ..... H01Q 15/08; H01Q 19/062; H01Q 15/02; H01Q 9/0485; H01Q 15/10
USPC ....................... 343/911 R, 754–758, 872–873
See application file for complete search history.

(56) References Cited

U.S. PATENT DOCUMENTS

| | | | | |
|---|---|---|---|---|
| 3,255,454 A * | 6/1966 | Walter et al. | | 343/754 |
| 3,656,165 A * | 4/1972 | Walter et al. | | 343/754 |
| 4,499,473 A * | 2/1985 | Rao | | 343/754 |
| 4,755,820 A * | 7/1988 | Backhouse et al. | | 343/700 MS |
| 5,781,163 A * | 7/1998 | Ricardi et al. | | 343/911 R |
| 5,900,847 A * | 5/1999 | Ishikawa et al. | | 343/909 |
| 6,246,369 B1 * | 6/2001 | Brown et al. | | 343/700 MS |
| 6,590,544 B1 * | 7/2003 | Filipovic | | 343/753 |
| 7,253,789 B2 * | 8/2007 | Kingsley et al. | | 343/911 R |
| 7,382,331 B2 * | 6/2008 | Kurashima et al. | | 343/911 L |
| 2006/0017637 A1 * | 1/2006 | Howell et al. | | 343/754 |

* cited by examiner

*Primary Examiner* — Huedung Mancuso
(74) *Attorney, Agent, or Firm* — Canady & Lortz LLP; Bradley K. Lortz

(57) ABSTRACT

An antenna element suitable for integrated arrays at terahertz frequencies is disclosed. The antenna element comprises an extended spherical (e.g. hemispherical) semiconductor lens, e.g. silicon, antenna fed by a leaky wave waveguide feed. The extended spherical lens comprises a substantially spherical lens adjacent a substantially planar lens extension. A couple of TE/TM leaky wave modes are excited in a resonant cavity formed between a ground plane and the substantially planar lens extension by a waveguide block coupled to the ground plane. Due to these modes, the primary feed radiates inside the lens with a directive pattern that illuminates a small sector of the lens. The antenna structure is compatible with known semiconductor fabrication technology and enables production of large format imaging arrays.

19 Claims, 16 Drawing Sheets

DIELECTRIC COVERED PLANAR ANTENNAS

CROSS-REFERENCE TO RELATED APPLICATIONS

This application claims the benefit under 35 U.S.C. §119 (e) of the following U.S. provisional patent application, which is incorporated by reference herein:

U.S. Provisional Patent Application No. 61/221,695, filed Jun. 30, 2009, and entitled "DIELECTRIC COVERED PLANAR ANTENNAS AT SUBMILLIMETER WAVELENGTHS FOR TERAHERTZ IMAGING APPLICATIONS", by Gill et al.

STATEMENT OF GOVERNMENT RIGHTS

The invention described herein was made in the performance of work under a NASA contract, and is subject to the provisions of Public Law 96-517 (35 U.S.C. 202) in which the Contractor has elected to retain title.

BACKGROUND OF THE INVENTION

1. Field of the Invention

This invention relates to imaging planar antennas. Particularly, this invention relates to dielectric covered planar antennas for terahertz imaging applications.

2. Description of the Related Art

Large focal planes employing thousands of detectors are expected to be required in future astrophysics missions. However, in order to meet the power and mass requirements for such missions, new technology is needed. One applicable novel technology being developed involves the integration of a stack of semiconductor wafers to form a tunable terahertz receiver front end. In addition, terahertz imaging for security applications may also benefit from large heterodyne arrays. Furthermore, multimode corrugated feed horns have also shown very good pattern characteristics, although fabrication becomes difficult using such designs for very large focal planes at high frequencies.

One desirable solution applicable to these systems employs fabrication a monolithic array of antennas on a planar substrate. However, most planar antenna designs produce broad beam patterns, and therefore require additional elements for efficient coupling to the telescope optics, such as substrate lenses or micro-machined horns. See e.g. Rutledge et al., "Integrated-circuit antennas" Infrared and Millimeter-Waves. vol. 10, pp. 1-90, 1983 and Rebeiz, "Millimeter-Wave and Terahertz Integrated Circuit Antennas," IEEE Proceedings. vol. 80, No. 11, 1992, which are incorporated by reference herein. Although this does not necessarily preclude their use in large arrays, and indeed large arrays using substrate lenses are being investigated; the key issues for such development include resolving the manufacture and assembly of a large "fly's eye" array of lenses. See e.g., Buttgenbach, "An Improved Solution for Integrated Array Optics in Quasi-Optical mm and Submm Receivers: the Hybrid Antenna" IEEE MTT. vol 41, October 1993, which is incorporated by reference herein. While it is also possible to place an array of antennas behind a single lens, optical aberrations tend to limit the size of such an array design.

In view of the foregoing, there is a need in the art for apparatuses and methods for high frequency antenna designs. There is also a need for such apparatuses and methods to utilize cost-effective manufacturing such as with photolithographic techniques, e.g. a monolithic array produced on a planar substrate. There is particularly a need for such apparatuses and methods in imaging applications at terahertz frequencies. These and other needs are met by the present invention as detailed hereafter.

SUMMARY OF THE INVENTION

An antenna element suitable for integrated arrays at terahertz frequencies is disclosed. The antenna element comprises an extended spherical (e.g. hemispherical) semiconductor lens, e.g. silicon, antenna fed by a leaky wave waveguide feed. The extended spherical lens comprises a substantially spherical lens adjacent a substantially planar lens extension. A couple of TE/TM leaky wave modes are excited in a resonant cavity formed between a ground plane and the substantially planar lens extension by a waveguide block coupled to the ground plane. Due to these modes, the primary feed radiates inside the lens with a directive pattern that illuminates a small sector of the lens. The antenna structure is compatible with known semiconductor fabrication technology and enables production of large format imaging arrays.

A typical embodiment of the invention comprises an antenna including a substantially spherical lens having a base at a radius of the substantially spherical lens disposed adjacent to a substantially planar lens extension, and a substantially planar resonant cavity defined between a ground plane and a lower surface of the substantially planar lens extension. A feed for propagating a dominant TE10 mode is coupled to the resonant cavity at the ground plane. The substantially spherical lens may comprise a hemispherical lens and the base comprises a great circle of the hemispherical lens. In this case, the substantially planar lens extension may comprise silicon from a common wafer with the substantially spherical lens.

The substantially spherical lens and the substantially planar lens extension may each comprise a dielectric material. Typically, the substantially spherical lens and the substantially planar lens extension comprise silicon. The substantially spherical lens and the substantially planar lens extension may be contiguous and produced from a common dielectric material, e.g. silicon or quartz. In some embodiments, the cavity may comprise a dielectric material having a dielectric constant less than that of the substantially spherical lens and that of the substantially planar lens extension.

In some embodiments, the feed may be coupled to the resonant cavity by an iris through the ground plane, the iris substantially matching impedance to the dominant TE10 mode. The iris may comprise a double arc slot through the ground plane.

In further embodiments, the feed may be coupled to the resonant cavity at the ground plane along a normal axis through the substantially spherical lens. Alternately, the feed may be coupled to the resonant cavity at the ground plane substantially off a normal axis through the substantially spherical lens.

In a similar manner, a typical method embodiment for producing a planar dielectric antenna comprises the steps of etching from a dielectric material at least one substantially spherical lens having a base at a radius of the substantially spherical lens disposed adjacent to a substantially planar lens extension, forming a substantially planar resonant cavity between a lower surface of the substantially planar lens extension and a ground plane, and coupling a feed for propagating a dominant TE10 mode to the resonant cavity at the ground plane. Method embodiments of the invention may be further modified consistent with the apparatuses and systems described herein.

Another embodiment of the invention comprises an array of substantially spherical lenses each having a base at a radius of each of the substantially spherical lenses and each disposed adjacent to a substantially planar lens extension, and a substantially planar resonant cavity defined between a ground plane and a lower surface of the substantially planar lens extension. A feed for each of the substantially spherical lenses for propagating a dominant TE10 mode is coupled to the resonant cavity at the ground plane below each of the substantially spherical lenses. The array embodiments of the invention may be further modified consistent with the apparatuses and systems described herein.

BRIEF DESCRIPTION OF THE DRAWINGS

Referring now to the drawings in which like reference numbers represent corresponding parts throughout.

DETAILED DESCRIPTION OF THE PREFERRED EMBODIMENT

1. Overview

Figure 1A:
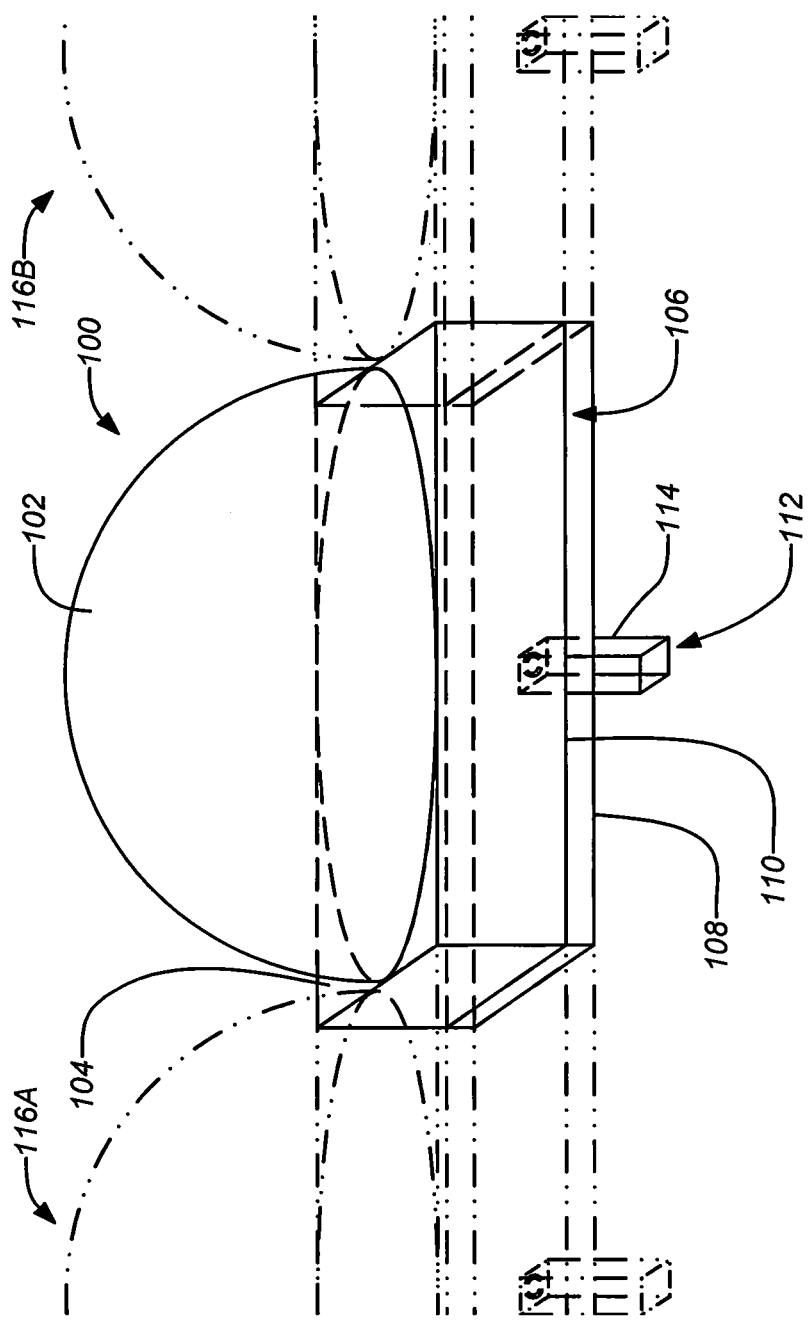
FIGS. 1A & 1B illustrate an example geometry for an antenna element embodiment of the invention.

As mentioned above, embodiments of the present invention are direct to a novel antenna suitable for integrated arrays at terahertz frequencies. The antenna may include a waveguide feed, which can be integrated with Schottky detectors and mixers, that excites a silicon lens antenna through a leaky-wave or electromagnetic band-gap (EBG) resonant cavity. The cavity is used to both match the waveguide feed with the silicon medium and to illuminate the upper part of the lens.

Embodiments of the invention effectively address the issues described above by using an integrated silicon micro lens which can potentially be fabricated using photolithographic techniques. See e.g., Lee et al., "A glass reflowed microlens array on a Si substrate with rectangular through-holes," J. Opt. A. 10 (2008) 044003, 2008, which is incorporated by reference herein. Example embodiments of the invention may employ an extended hemispherical lens antenna fed by a leaky wave feed. The primary feed may comprise a single mode waveguide which may be easily integrated with mixers and detectors such as Schottky diodes. Between the waveguide and the silicon lens, a resonant cavity exists where a couple of TE/TM leaky wave modes are excited. These modes allow the primary feed to radiate inside the lens with a more directive pattern. One primary advantage of this antenna structure applied to the terahertz band is related to the fabrication. Since only a small sector of the lens is required (e.g. approximately 15°), the lens may be easy to micro-fabricate. This can enable the fabrication of an entire array of lenses on a common wafer. Thus, the array of primary feeds, e.g. including waveguide, slot iris and air cavity, may be fabricated in a single silicon wafer by using a three-step etching process.

A typical lens feed design for an embodiment of the invention is different than that described in Llombart et al., "Impact of Mutual Coupling in Leaky Wave Enhanced Imaging Arrays", IEEE Trans. on AP, vol. 56, no. 4, pp. 1201-1206, April 2008, which is incorporated by reference herein, because it radiates inside the dielectric instead of into free space. The idea of using EBG enhanced feeds in combination with dielectric lenses was proposed in Neto et al.,"EBG enhanced dielectric lens antennas for the imaging at sub-mm waves", IEEE Antennas and Propagation Society International Symposium, 2008. AP-S 2008, July 2008, which is incorporated by reference herein, where an inverted EBG configuration was used to enhance the out of focus feed performance. Typically in standard leaky-wave or EBG antennas, the directivity of a small antenna is considerably enhanced due to the excitation of a couple of leaky wave modes. See Jackson et al., "A leaky-wave analysis of the high-gain printed antenna configuration", IEEE Trans. Antennas and Propagation, vol. 36, no. 7, pp. 905-909, July 1988, which is incorporated by reference herein. However, the drawback is that their fractional bandwidth (BW) is inversely proportional to the achievable directivity, and therefore a very directive antenna comes at the cost of a very narrow BW. See Neto et al., "EBG enhanced feeds for the improvement of the aperture efficiency of reflector antennas", IEEE Trans. Antennas and Propagation, Vol. 55, no.8, August 2007, pp. 2185-2193, which is incorporated by reference herein.

However, with embodiments of the present invention, the directivity depends on the diameter of the lens and not on the leaky wave cavity. In one example, a leaky wave feed radiates a very directive pattern inside the dielectric with a taper of 10 dB at approximately 15°. As a result only about 30° of the lens surface is actually illuminated. The upper part of the lens presents only a small curvature and because of that the antenna with the lens may be fabricated photolithographically. This makes it possible to fabricate an array of lens antennas integrated on a single wafer. Moreover, the fabrication of the lens primary feed is compatible with silicon micromachining techniques. See e.g., Chattopadhyay et al., "Deep Reactive Ion Etching based silicon micromachined components at terahertz frequencies for space applications", 33rd International Conference on Infrared, Millimeter and Terahertz Waves, 2008, 15-19 Sep. 2008, which is incorporated by reference herein. Therefore, an array of microlenses and feeds can be fabricated on separate silicon wafers such that the assembly of an antenna array may be achieved by simply stacking and aligning two wafers.

2. Exemplary Antenna Geometry and Feed Design

Figure 1B:
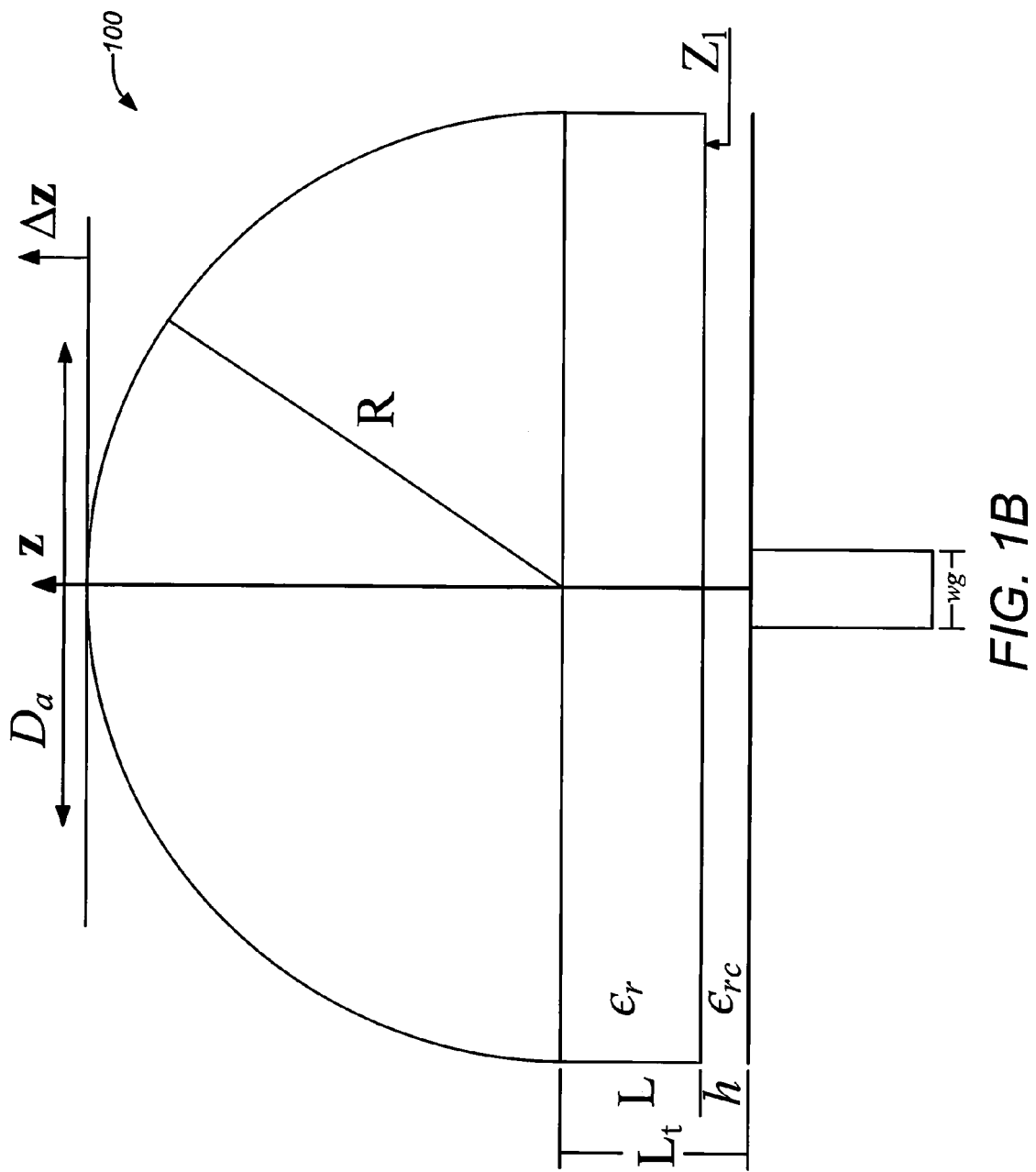

FIGS. 1A & 1B illustrate an example geometry for a dielectric planar antenna element 100 embodiment of the invention. The feed 112 for the exemplary antenna element 100 may comprise a square waveguide 114 propagating the dominant TE10 mode. An extended spherical lens of the antenna element 100 comprises a substantially spherical lens 102 having a base at a radius of the substantially spherical lens disposed adjacent to a substantially planar lens extension 104. A substantially planar resonant cavity 106 is defined between a ground plane 108 and a lower surface 110 of the substantially planar lens extension 104. The feed 112 for propagating a dominant TE10 mode is coupled to the resonant cavity at the ground plane 108, typically along a normal axis through a center of the spherical lens 102. It should be noted that although the spherical lens 102 is typically hemispherical as shown, a much smaller portion of the lens (e.g. approximately only 30°) is illuminated in a typical application. Accordingly, a functional antenna element 100 may not require the full hemisphere of the lens. In any case, however, the spherical lens has a base at the radius of the sphere adjacent to the planar lens extension 104. It should also be noted that in general the lens 102 is produced along with the lens extension 104 from a contiguous material. For example, a silicon lens will typically be produced along with a silicon lens extension as contiguous element or a quartz lens along with a quartz lens extension. However, in some applications alternate materials may be employed for at least a portion of the extension, e.g. a silicon lens and a quartz lens extension. In addition, the antenna element 100 is most efficiently constructed and employed an array comprising multiple additional antenna elements 116A, 116B (two- or three-dimensional). In this case, the spherical lenses 102, planar lens extension 104, ground plane, cavity and/or feeds may utilize common structural elements produced from known semiconductor manufacturing techniques, such as photolithography.

FIG. 1B shows an example geometry for a dielectric planar antenna element 100 embodiment of the invention defining variable dimensions and other parameters discussed herein. The antenna comprises an extended spherical lens (hemispherical as shown) defined with the radius R, the dielectric constant $\in_r$ (for both the lens 102 and the extension 104 materials) and the extension height L; a resonant cavity of thickness h and dielectric constant $\in_{rc}$. A double slot iris is etched through the ground plane 108; and this iris is excited by the square waveguide 114 having side dimension wg.

Figure 1C:
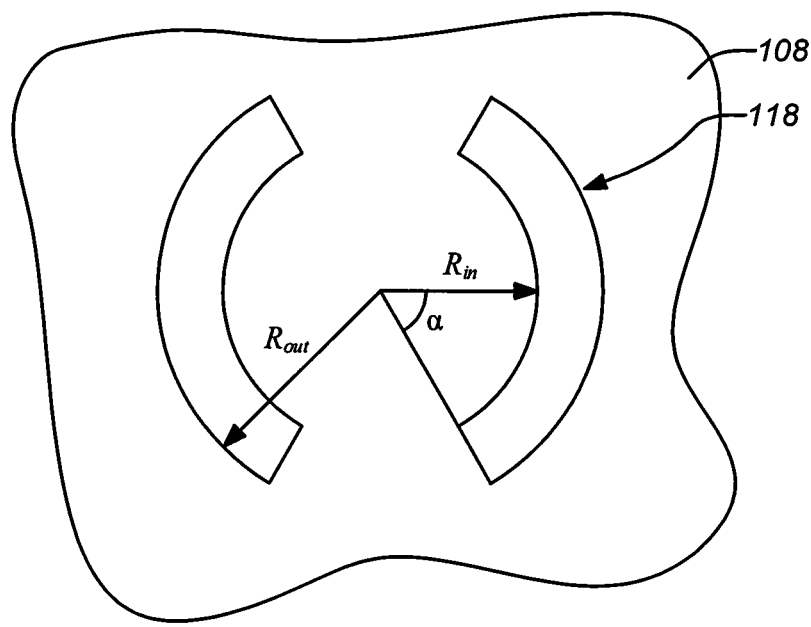
FIG. 1C illustrates an example double slot iris for the waveguide of the antenna element embodiment of the invention.

This waveguide 114 may be loaded with a double slot iris 118 through the ground plane 108 as illustrated in FIG. 1C where dimensional parameters for defining a double slot iris 118 are shown. The double slot iris 118 may be designed to match the antenna impedance to the TE10 mode as well as to suppress undesired modes that can propagate in the cavity. See e.g. Llombart et al., "Impact of Mutual Coupling in Leaky Wave Enhanced Imaging Arrays", IEEE Trans. on AP, vol. 56, no. 4, pp. 1201-1206, April 2008, which is incorporated by reference herein.

Between the waveguide feed and the dielectric lens, there is a cavity of dimension h and dielectric constant $\in_{rc}$. See FIG. 1B. This cavity acts as a partially guiding structure where leaky wave modes can propagate. These modes present a complex propagation constant $k_{lw}$ and defines the field distribution of the radiating aperture at the antenna. The leaky wave modes radiate in a direction defined by the real part of their propagation constant, while the imaginary part is related to the field attenuation at the aperture. A couple of TE/TM leaky wave modes pointing towards broadside can be excited when $\in_{rc} < \in_r$ and $h = 0.5\lambda_0/\sqrt{\in_{rc}}$. Finally, an extended hemispherical lens, defined with the extension height L and the radius R, is disposed on top of the cavity. The primary feed is designed to excite only the central part of the dielectric lens such that only a small curvature of the lens is required and that can be fabricated photolithographically.

In dielectric super-layers or leaky wave antennas, the propagation constant of the leaky wave modes depends on the impedance that is seen from the top of the cavity $Z_l$ identified in FIG. 1B. See e.g. Neto et al., "Wide band localization of the dominant leaky wave poles in dielectric covered antennas", IEEE AWPL, vol. 5, pp. 549-551, December 2006, which is incorporated by reference herein. The higher the directivity, the lower the impedance $Z_l$ must be. A low impedance is typically generated using a quarter wavelength dielectric stratification.

Llombart et al., "Impact of Mutual Coupling in Leaky Wave Enhanced Imaging Arrays", IEEE Trans. on AP, vol. 56, no. 4, pp. 1201-1206, April 2008, which is incorporated by reference herein, describes a dielectric quartz super-layer with a quarter wavelength thickness. In that case $Z_l = \zeta_0/\in_{rq}$, with $\in_{rq} = 4.45$ and $\zeta^0$ being the free space impedance. The pointing direction of the leaky wave modes can be derived from the real part of the propagation constant as $\theta = \sin^{-1}(\text{Re}[k_{lw}/k_0])$, where $k_0$ is the free space propagation constant. $\theta$ is approximately 17° for that case. If a more directive antenna is required, the impedance $Z_l$ must be smaller; this corresponds to higher dielectric constant but at the cost of reducing the impedance BW. See Neto et al., "EBG enhanced feeds for the improvement of the aperture efficiency of reflector antennas", IEEE Trans. Antennas and Propagation, Vol. 55, no. 8, August 2007, pp. 2185-2193, which is incorporated by reference herein.

For embodiments of the present invention, rather than a dielectric super-layer stratification, an infinite layer of dielectric is modeled. Thus, the impedance seen on top of the cavity is $Z_l = \zeta_0/\sqrt{\in_r}$. The impedances associated with the quartz super-layer and the infinite silicon layer are very similar sincere $\sqrt{\in_{rs}} \approx \in_{rq}$, with $\in_{rs} = 11.9$, and therefore the associated leaky wave propagation constants are also similar.

Figure 2:
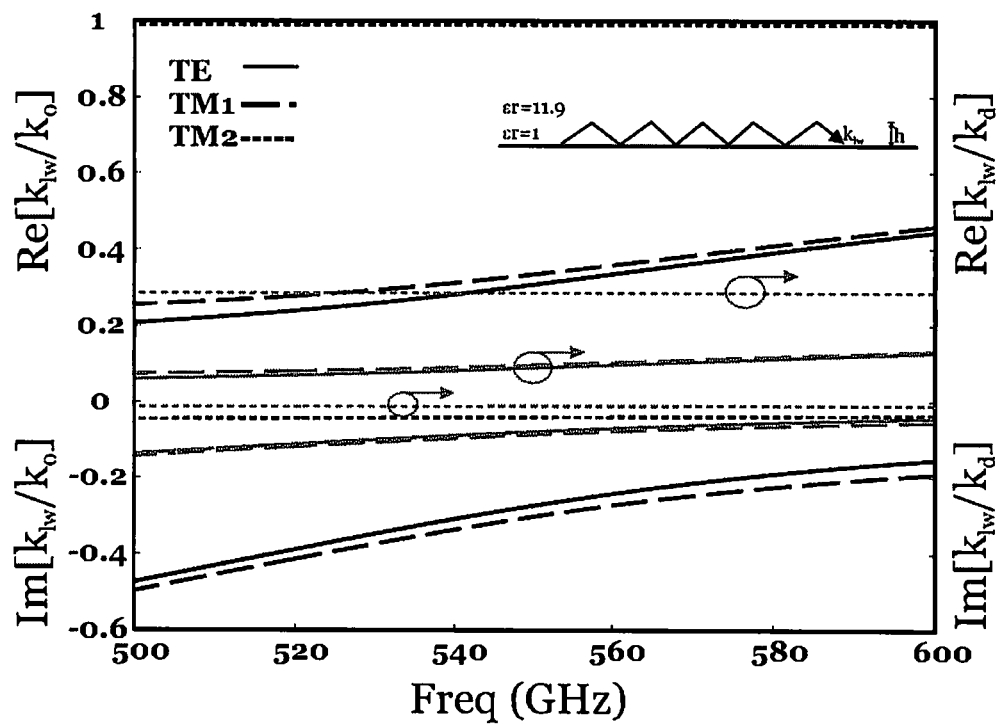
FIG. 2 shows the real and imaginary parts of the propagation constant of the leaky wave modes present in an example air cavity between a ground plane and an infinite silicon medium.

FIG. 2 shows the real and imaginary parts of the propagation constant $k_{lw}$ of the leaky wave modes present in an example air cavity (h=275 μm) between a ground plane and an infinite silicon medium. (It should be noted that "infinite" as used herein merely indicates a relative mathematical requirement as will be understood by those skilled in the art.) There are three possible modes, two TM and one TE. The mode $TM_2$ is a non-desired mode because it radiates towards large angles. On the left axis of the plot of FIG. 2, the propagation constants are normalized to the free space propagation constant $k_0$. These values are very similar to the ones of a quartz quarter wavelength super-layer, and the pointing angles are relatively large, e.g. 17°. However, the calculated pointing angles inside the dielectric, from the right axis of the figure, where the propagation constant is normalized to $k_d = k_0 \sqrt{\in_r}$ instead of $k_0$, reveal values of approximately 6°, which correspond to a directive pattern within the dielectric medium. On the left axis, $k_{lw}$ is normalized to the free space propagation constant, $k_0$, whereas $k_{lw}$ is normalized to the propagation constant in the dielectric, $k_d=k_0\sqrt{\in_r}$, on the right axis.

The improvement in terms of pointing direction of the leaky wave between silicon and air was proposed for the first time by Neto, "Planar Implementation of the UWB Leaky Lens Antenna", in ICEAA 2009, Sep. 14-18 Torino, Italy, which is incorporated by reference herein. A non-resonant air cavity was used to change the pointing angle of a leaky wave emanating from a long slot. Another advantage of embodiments of the present invention is that the leaky wave mode shows very similar frequency behavior as the quartz superlayer, and therefore will have similar antenna impedances. Finally, those skilled in the art will also appreciate that further embodiments of the invention may be developed using different dielectric combinations, e.g. infinite quartz layer (lens extension), quartz cavity and silicon lens, depending on the tradeoffs between the bandwidth and the illumination of the microlens for a particular design. Although typically the cavity is air (or vacuum), the cavity may comprise a dielectric material provided the $\in_{rc}$ of the cavity material is less than that of the lens (and lens extension). Thus, a quartz lens (and extension) may use an air cavity, whereas a silicon lens (and extension) may use a quartz cavity.

As previously stated, in dielectric super-layer antennas, there are three leaky wave modes that can propagate, two TM and one TE. See e.g., Neto et al., "EBG enhanced feeds for the improvement of the aperture efficiency of reflector antennas", IEEE Trans. Antennas and Propagation, Vol. 55, no. 8, August 2007, pp. 2185-2193, which is incorporated by reference herein. The main TE/TM modes point towards broadside, while the second TM mode points to larger angles. The second TM mode, also shown in FIG. 2, alters the radiation pattern at large angles and should be suppressed. This suppression may be achieved by either using a larger waveguide size or by using a double slot iris. The double slot iris solution is more convenient because it also helps to match the reflection coefficient of the antenna to the impedance of the TE10 mode of the waveguide.

Figure 3:
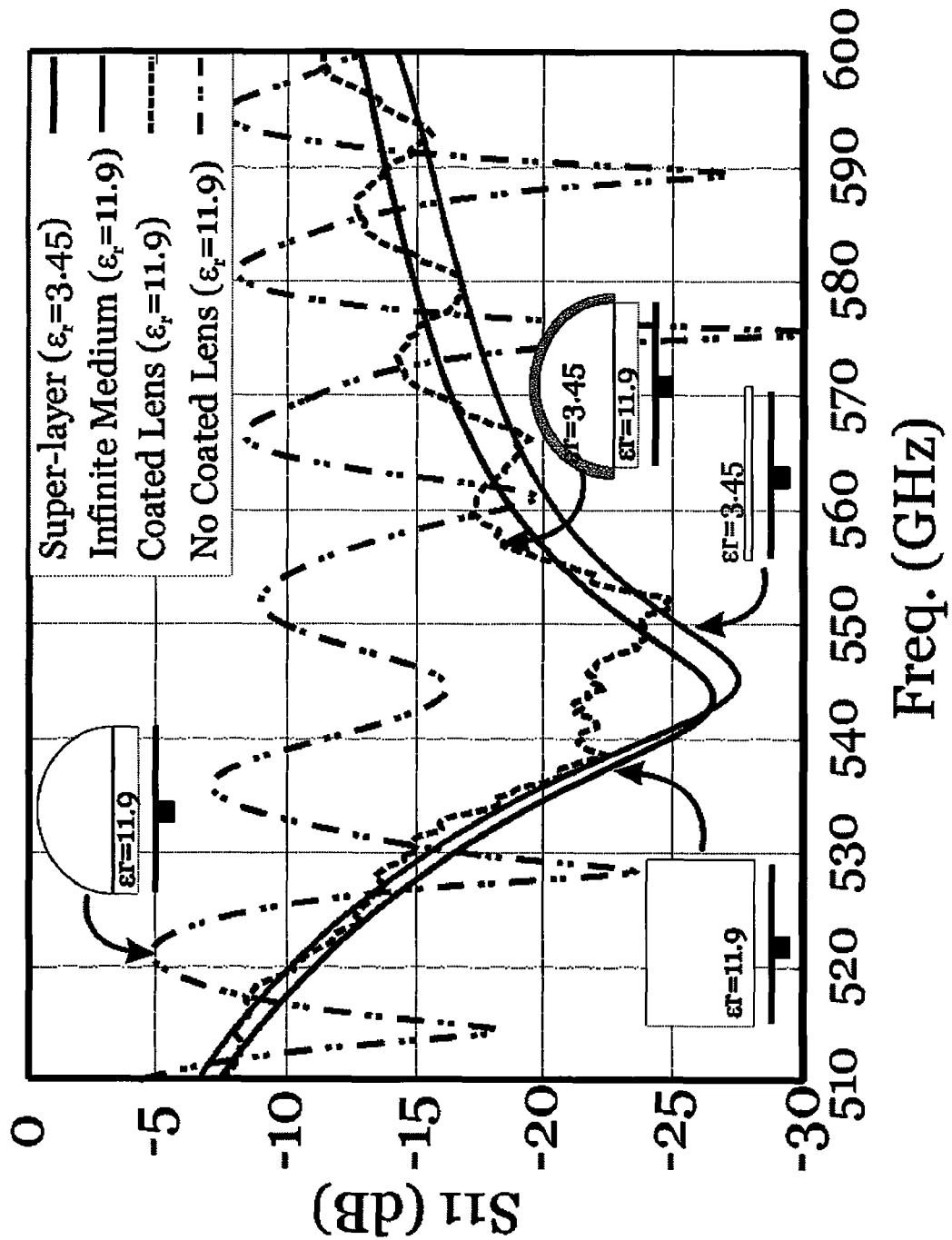
FIG. 3 shows a simulated reflection coefficient of a square waveguide loaded by a double slot iris in the presence of a resonant air cavity.

FIG. 3 shows a simulated reflection coefficient of a square waveguide loaded by a double slot iris in the presence of a resonant air cavity. See Computer Simulation Technology Microwave Studio (CST MWS), Darmstadt, Germany User Manual Version 5.0, which is incorporated by reference herein. The input reflection coefficient of a waveguide loaded with a double arc iris in presence of an air cavity (h=275 µm) is shown where the feed dimensions are, Rin=109.7 µm, Rout=192 µm, α=50° and ωg=367.6 µm (as shown in FIG. 1B). Several cases are shown on top of the cavity: a quartz quarter wavelength super-layer ($\sqrt{\in_{rs}}\approx\in_{rq}$); an infinite silicon medium ($\in_{rs}$=11.9); and an extended hemispherical lens with R=6 mm and L=−0.05R with and without a coating layer. In one example, a coating layer material for a silicon lens may be parylene, whereas a quartz lens, a coating layer material may be PTFE (i.e. Teflon®). Those skilled in the art will appreciate that other suitable materials for coating layers may be selected, e.g. meeting a required $\in_r$ of approximately 3.45. The cavity and feed dimensions remain common in all of them. An infinite silicon dielectric medium or a quartz quarter wavelength super-layer on top of the cavity produce very similar reflection coefficients in both configurations since they both present very similar load impedances $Z_1$.

FIG. 3 also shows the reflection coefficient in presence of an extended hemispherical lens that has been simulated with CST MWS including a quarter wavelength matching layer of $\in_r$=3.45. If a coating layer is not used, those skilled in the art will consider the multiple reflections that can have important effect on the reflection coefficient. See e.g., Neto et al., "Reflections inside an elliptical dielectric lens antenna", IEEE Proceedings on Microwaves, Antennas and Propagation, vol. 145, no. 3, pp. 243-247, June 1998, which is incorporated by reference herein. FIG. 3 shows where the input reflection coefficient for the same lens without a coating layer is shown. (Note that the silicon material is shown simulated without losses). In standard designs, the extension height may be around L=0.39R and the lens surface resembles the one of an elliptical lens. See Filippovic et al., "Double Slot on Extended Hemispherical and Elliptical Silicon Dielectric Lenses", IEEE Trans. on MTT, Vol. 41, no. 10, October 1993, which is incorporated by reference herein. In such cases, the reflections from the lens will arrive to the feed after two bounces with power reduced by around 75% in each reflection. However, when L<0.32R, the reflections can have a much stronger impact if they come directly back to the feed because they will be less attenuated than after a double reflection.

The lens is illuminated by the fields radiated from the leaky wave feed. This illumination pattern affects the directivity and aperture efficiency of the lens, which are of major importance when considering an array. The primary fields may be computed in order to use them as an input to a physical optics (PO) method. The radiation fields can be derived analytically for a square waveguide by using the spectral Green's Function.

Figure 4A:
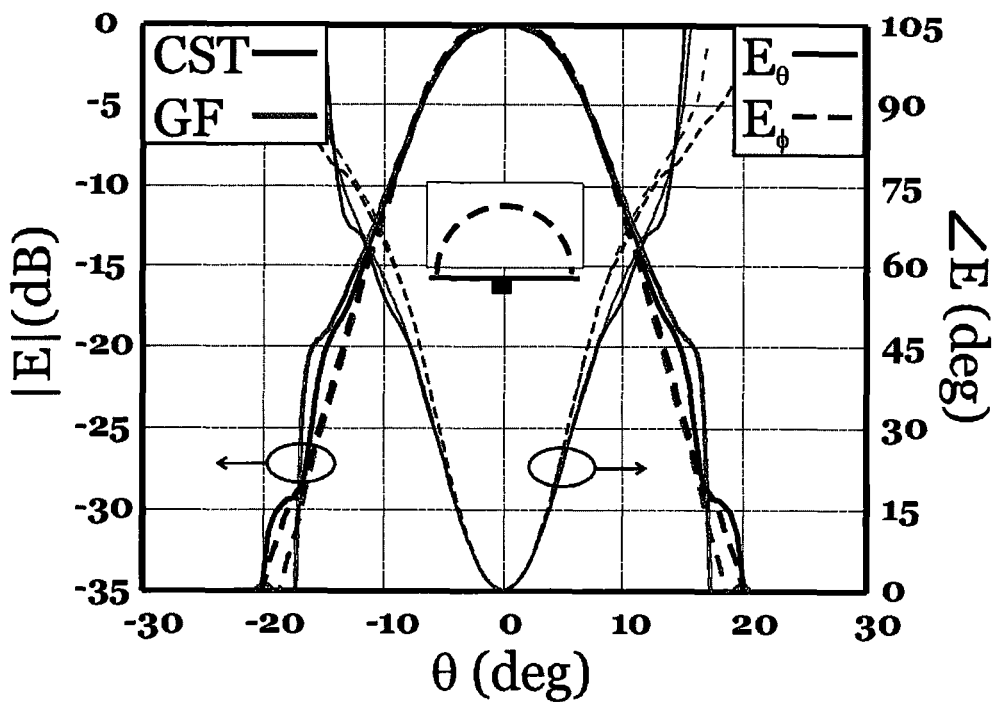
FIGS. 4A & 4B show a comparison of two example simulations of the far and near fields inside the dielectric medium.
Figure 4B:
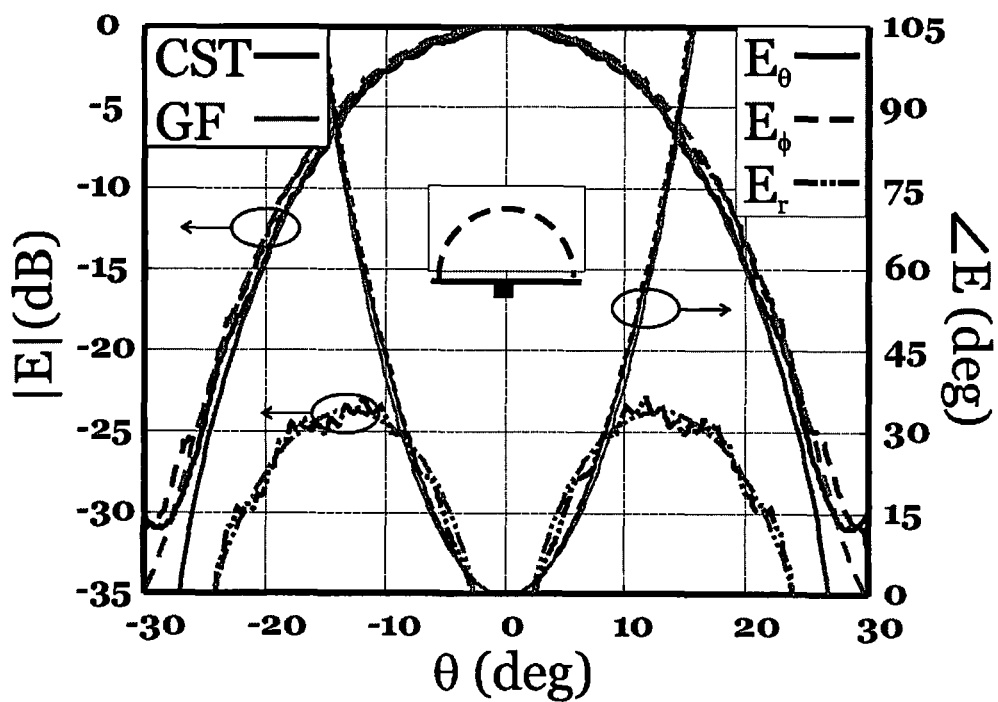

FIGS. 4A & 4B show a comparison of the Green's function calculation and the CST MWS simulation of the far and near (at 2.7 mm) fields inside the dielectric medium for a waveguide feed with ωg=521.9 µm and f=545 GHz. FIG. 4A show the comparison between the far fields computed analytically and those derived from an example CST MWS simulation. See again, Neto et al., "EBG enhanced feeds for the improvement of the aperture efficiency of reflector antennas", IEEE Trans. Antennas and Propagation, Vol. 55, no. 8, August 2007, pp. 2185-2193, which is incorporated by reference herein. These far fields are actually very similar to the ones associated with the iris if the correct waveguide dimension is chosen. The fields shown in FIG. 4A are computed in the far field of the feed. However, depending on the final geometry of the particular antenna design, the lens surface may be in the near field of the feed. In this case, the primary fields used for the lens PO design method should be the near fields in order to achieve accurate results. These fields can be computed by pre-tabulating the Green's function in the space domain (ρ and φ) and by doing a spatial summation over the iris aperture. See Llombart, "Development of integrated printed array antennas using EBG substrates", Ph.D. Thesis, May 2005, Universidad Politecnica de Valencia, which is incorporated by reference herein.

FIG. 4B shows the comparison of computed near field at z=2.7 mm and the one simulated with CST. The near fields are shown broader than the far fields. Accordingly, the taper angle associated to a certain field level (e.g. 10 dB) will differ if the feed is in the near or far field, and this will affect the associated microlens sector dimension. The fields in FIG. 4B are associated with the radiative near-field region of the feed where the r-component is small enough to ignore it in the PO calculations, and the main difference with the far field is associated to a broader field taper. Those skilled in the art will appreciate that the fields shown in the figure are very directive inside the dielectric due to the leaky wave cavity. The lens primary feed is compatible with silicon micro-machined fabrication techniques. The waveguide, slot iris and air cavity may be fabricated in the same silicon wafer by using a three-step micro-machining. Those skilled in the art will appreciate that other kinds of known directive antennas may be used to illuminate the lens, although they may be more difficult to fabricate or present higher losses. The weakness of the leaky wave feed is its frequency behavior due to the variation of the leaky wave propagation constant. A relatively small dielectric contrast may be used in order to work in a 10% BW. The feed fields present a relatively low frequency variation in this frequency range. The dielectric constant may be further reduced in order to improve the BW at the cost of increasing the illuminated lens sector.

A significant aspect is the phase of the fields shown in FIGS. 4A & 4B. They are computed from the waveguide aperture, and it can be seen that the phase center is not in this plane, and is actually below the waveguide aperture. Moreover, the phase center of the radiative near-fields is not the same as the far field. This fact implies that the extension of the lens has to be changed from the standard case in order to compensate for the phase difference, as will be shown hereafter.

After determining the radiation patterns inside the dielectric medium, the lens secondary patterns may be calculated by using standard PO techniques as described in Filippovic et al., "Double Slot on Extended Hemispherical and Elliptical Silicon Dielectric Lenses", IEEE Trans. on MTT, Vol. 41, no. 10, October 1993.

Figure 5A:
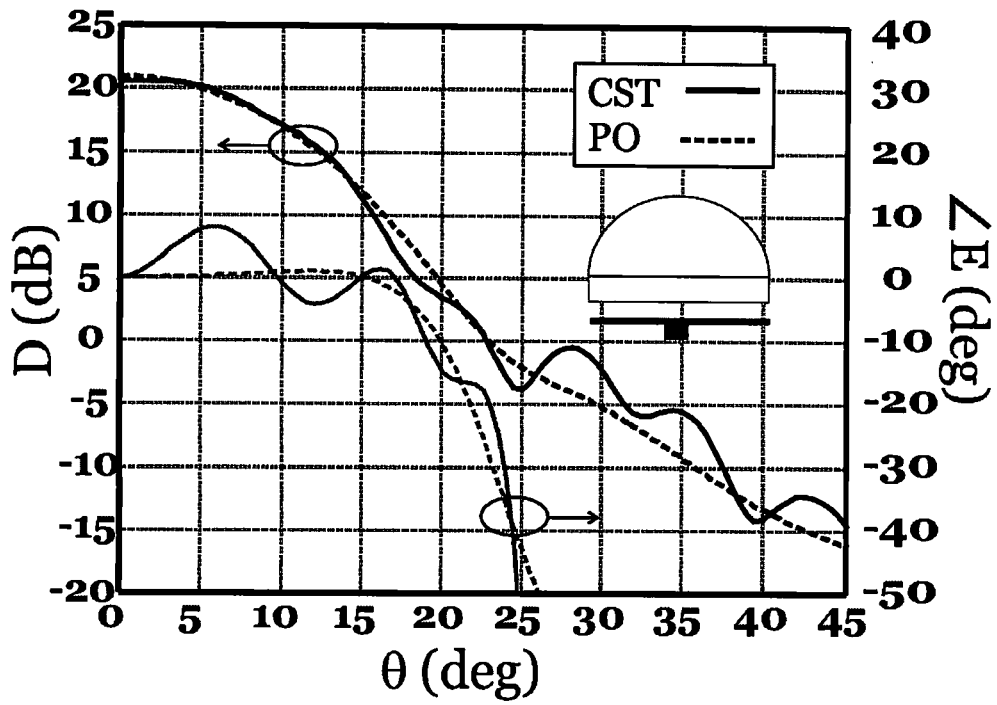
FIGS. 5A & 5B show the secondary patterns for a silicon lens with R=3 mm and L=R simulated for the E-plane and the H-plane.
Figure 5B:
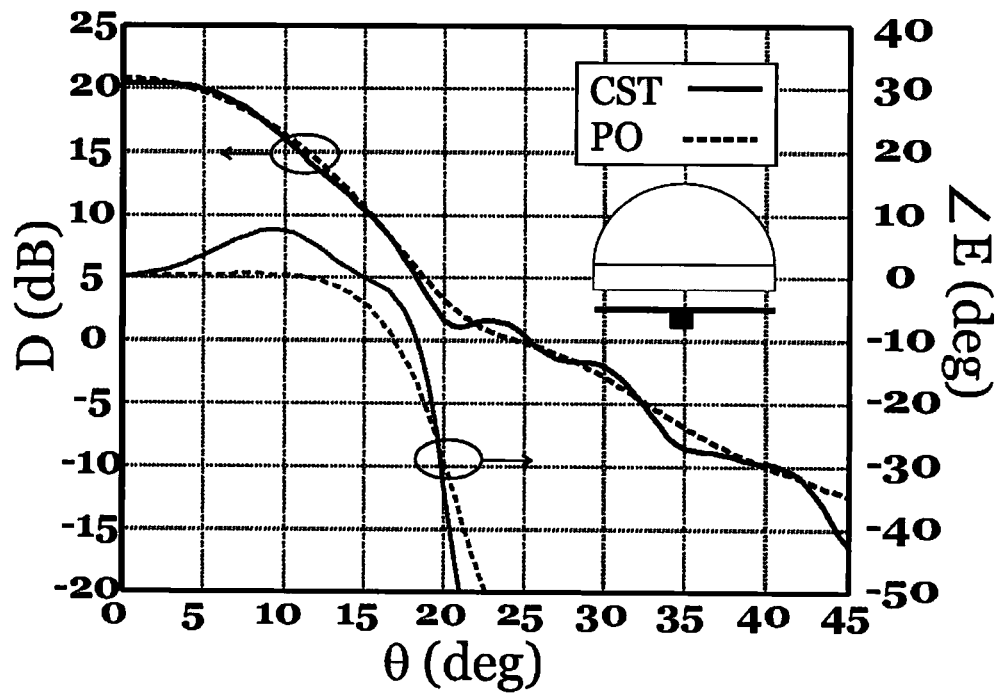

FIGS. 5A & 5B show the secondary patterns for a silicon lens with R=3 mm and L=R simulated with both CST MWS and the PO method. FIG. 5A shows the E-plane and FIG. 5B shows the H-plane. The CST geometry includes a coating layer. As shown, there is very good agreement between both simulations. The phases are plotted with the reference on top of the lens surface, as shown in FIG. 1B.

Figure 6A:
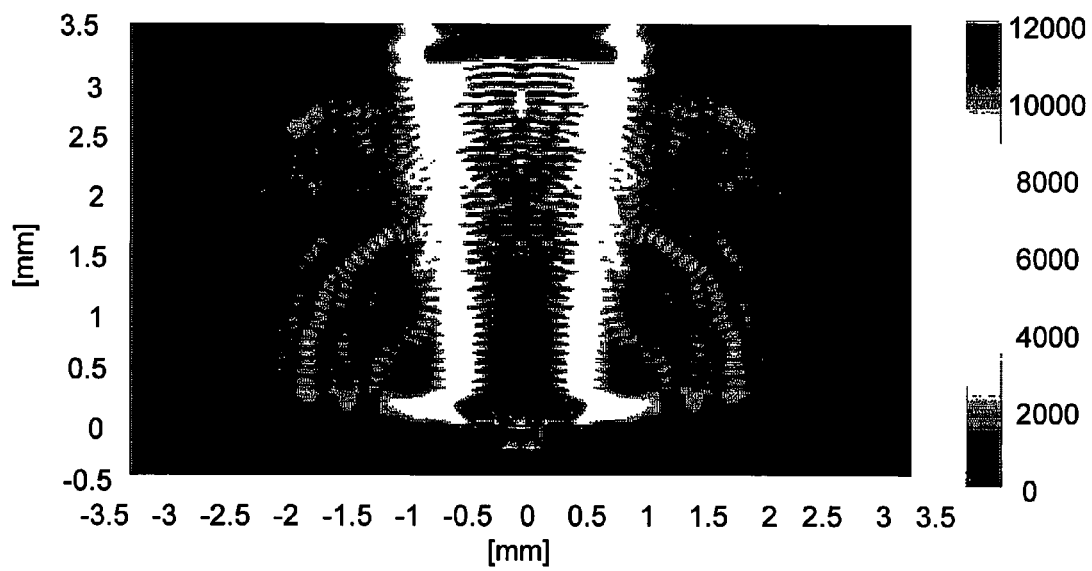
FIGS. 6A & 6B show a simulated electric field inside the lens of FIGS. 5A & 5B.
Figure 6B:
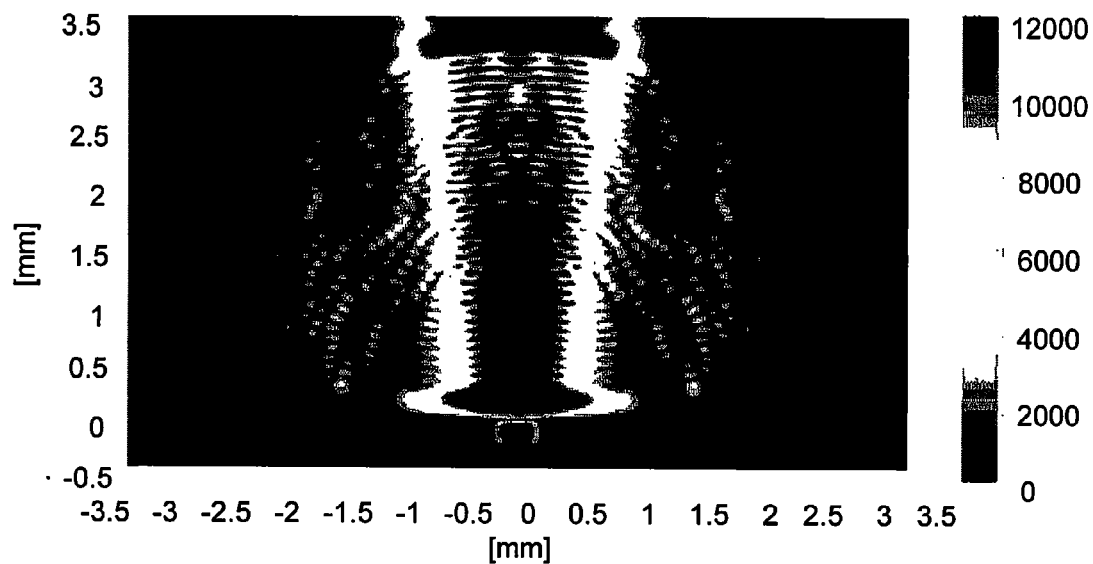

FIGS. 6A & 6B show the electric field inside the lens of FIGS. 5A & 5B simulated with CST MWS. One can clearly appreciate that only a small sector lens is actually illuminated. The magnitude of the electric field inside the lens is shown for the E-plane in FIG. 6A, and the H-plane in FIG. 6B.

Extended hemispherical lenses have been widely used with planar antennas in the Terahertz band. For such antennas, the phase center of the primary feed is in the same plane as the planar antenna. In this case, the optimum lens shape that will provide well-focused patterns is an ellipsoidal lens with the eccentricity being $\sqrt{\overline{\epsilon_r}}$, which can be derived by performing a geometrical tracing from the rays emanating from one of its foci. Extended hemispherical lenses can synthesize elliptical lenses by carefully choosing a particular extension length. For silicon lenses, this optimum height is around 0.33R and the surface difference between the ellipsoidal and extended hemispherical lens is very small. When the actual phase center of the antenna is not in the antenna aperture plane, the optimum extension height of the lens can differ considerably from the geometrical one as it is the case here.

The optimum height can be determined in terms of the directivity and Gaussicity of the secondary lens patterns. Different lens diameters, as well as the frequency behavior may also be considered. As a primary field, the near fields of the actual iris loaded waveguide may considered by pre-tabulating the Green's function and using the iris spatial currents simulated with MW CST for an infinite silicon medium.

Figure 7:
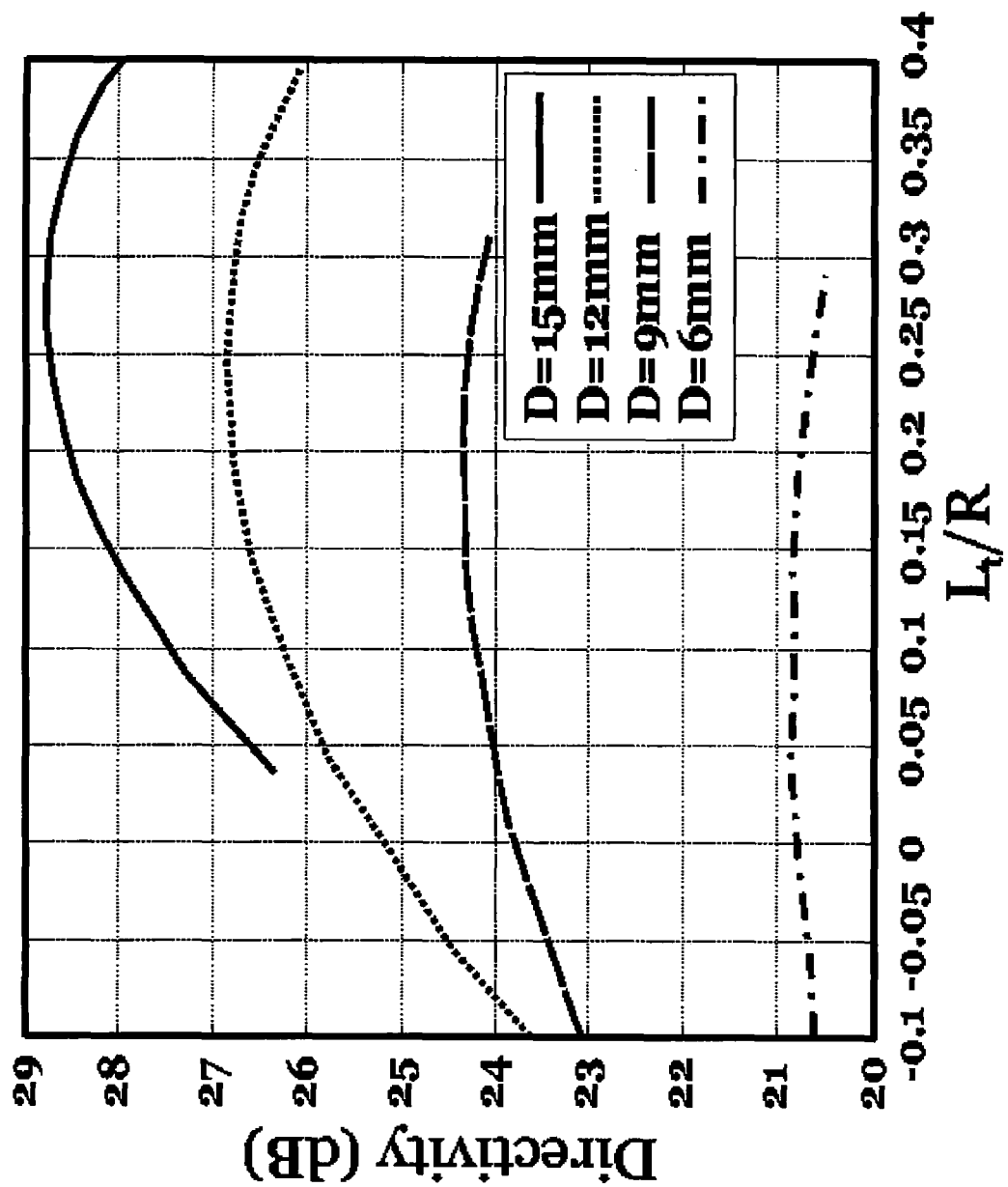
FIG. 7 shows directivity as a function of the lens extension at the central frequency (545 GHz) for several example lens diameters.

FIG. 7 shows the simulated directivity as a function of the lens extension (L) for four different example lens diameters: 2R=6 mm, 9 mm, 12 mm and 15 mm at the central frequency (545 GHz). In none of the cases, the maximum directivity extension is at the conventional extension. This is a consequence of the phase variation of the primary feeds shown in the previous section. Moreover, the optimum extension depends on the actual lens diameter due to the fact that the lens illumination varies both in amplitude and phase depending on the near-field distance to the lens surface. Even so, the extension heights associated to the maximum directivity in FIG. 7 approaches the standard case for large diameters, where the phase variation of the feed is less important as the diameter of the lens is increased.

Figure 8:
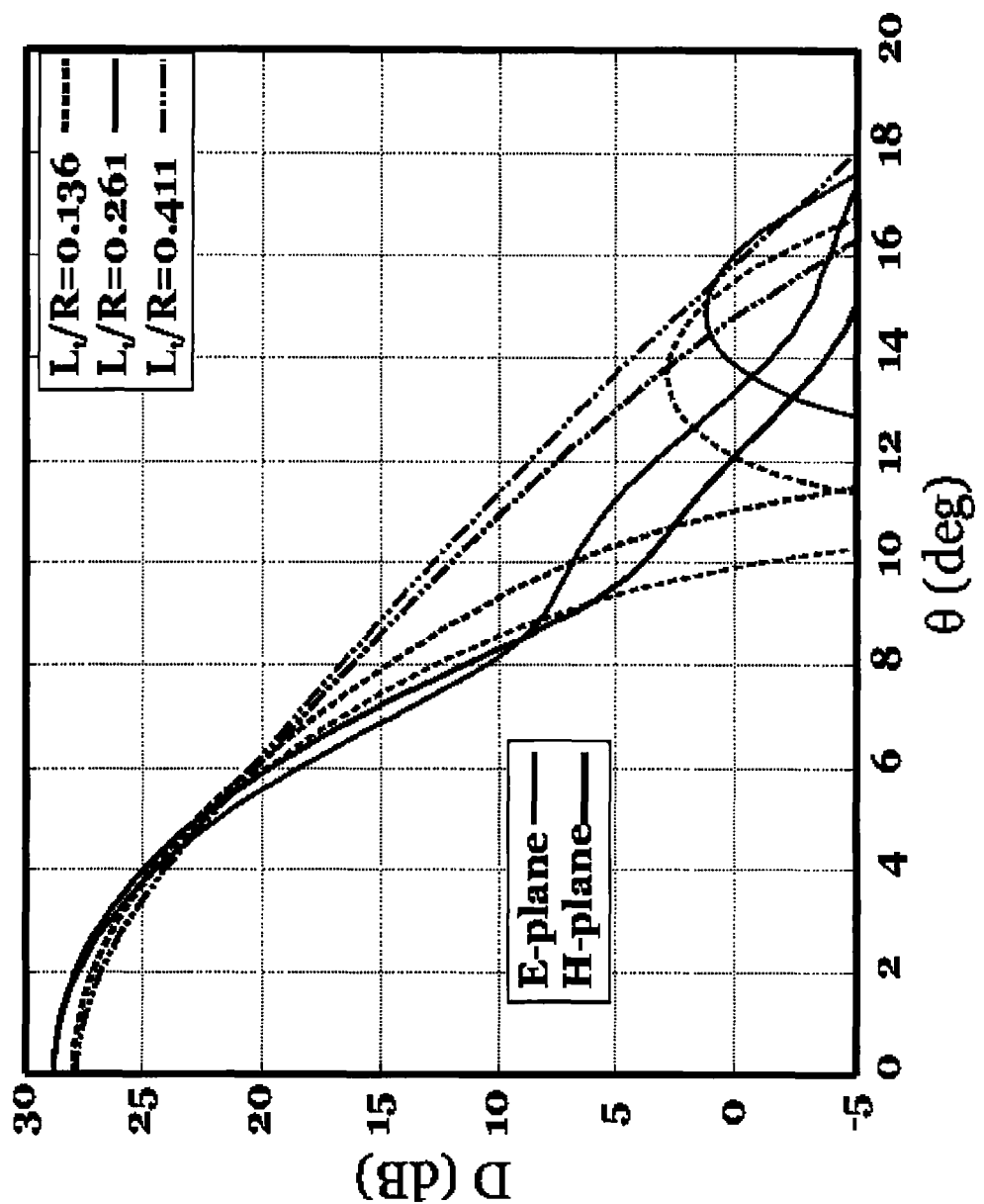
FIG. 8 shows lens secondary patterns for several example extension heights and 2R=15 mm.

For all the cases shown in FIG. 7 the secondary fields present very high values (over 97%) of Gaussicity, which is defined as the coupling efficiency of a far-field pattern of an antenna to the far-field pattern of a Gaussian-beam, due to the very low aperture efficiency. FIG. 8 shows the secondary patterns for 2R=15 mm and several example extension height values. The fields present very good rotational symmetry as well as low side lobes and therefore high Guassicity values. The very low aperture efficiency is a consequence of the objective of illuminating a very small sector of the lens.

Figure 9:
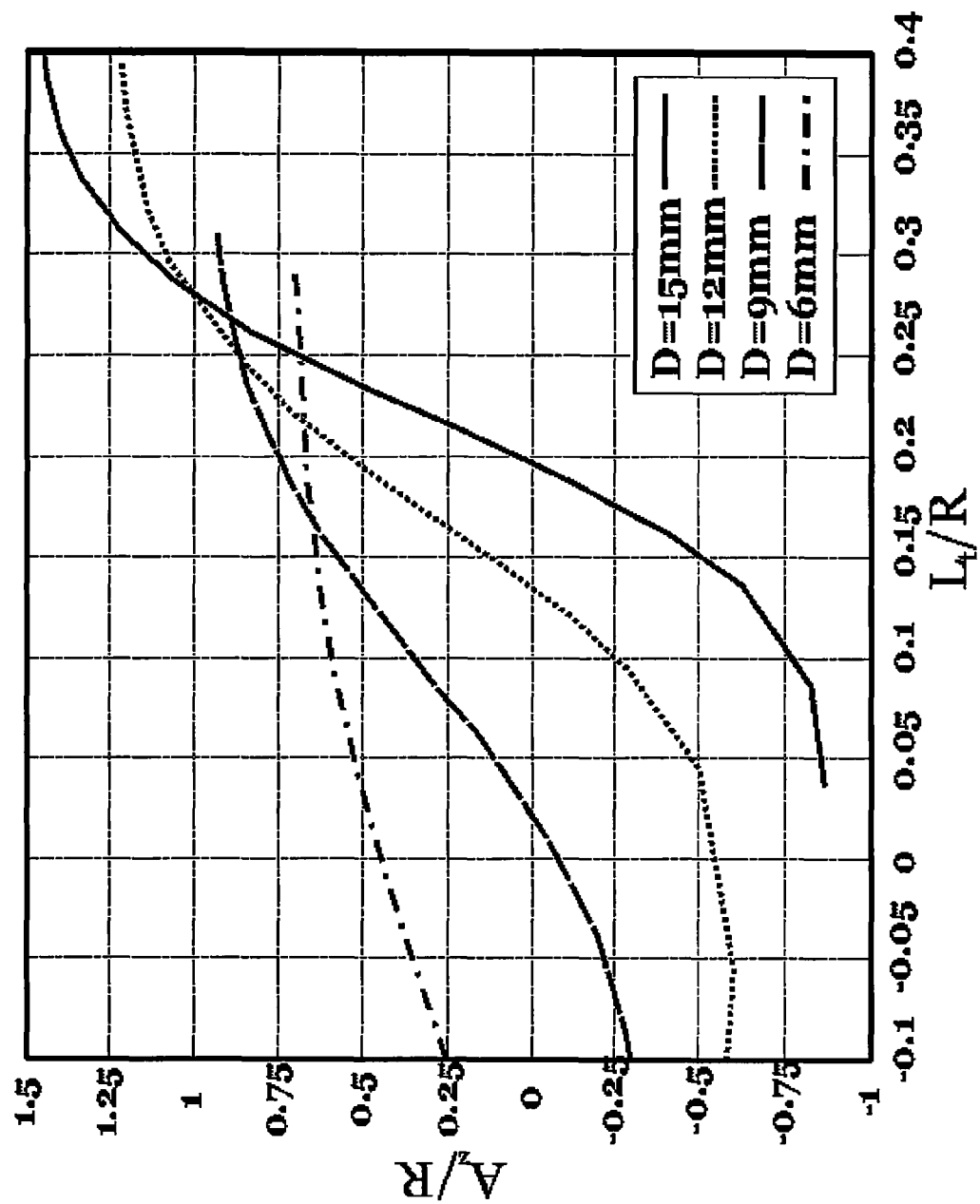
FIG. 9 shows the ratio between the displacement of the phase center, $\Delta z$ and the lens diameter.

The phases plotted in FIG. 5 are relatively flat indicating that the phase center of the lens at the top of the lens surface. This differs from standard designs implemented with planar antennas, where the phase center is at the origin of the hemisphere. This displacement of the phase center is also introduced by the feed phase (see FIG. 4). FIG. 9 plots the phase center, which is calculated in order to maximize the Gaussicity, for all cases shown in FIG. 5. After determining the optimum lens extension for a particular lens diameter, an analysis of the frequency behavior can be performed.

Figure 10:
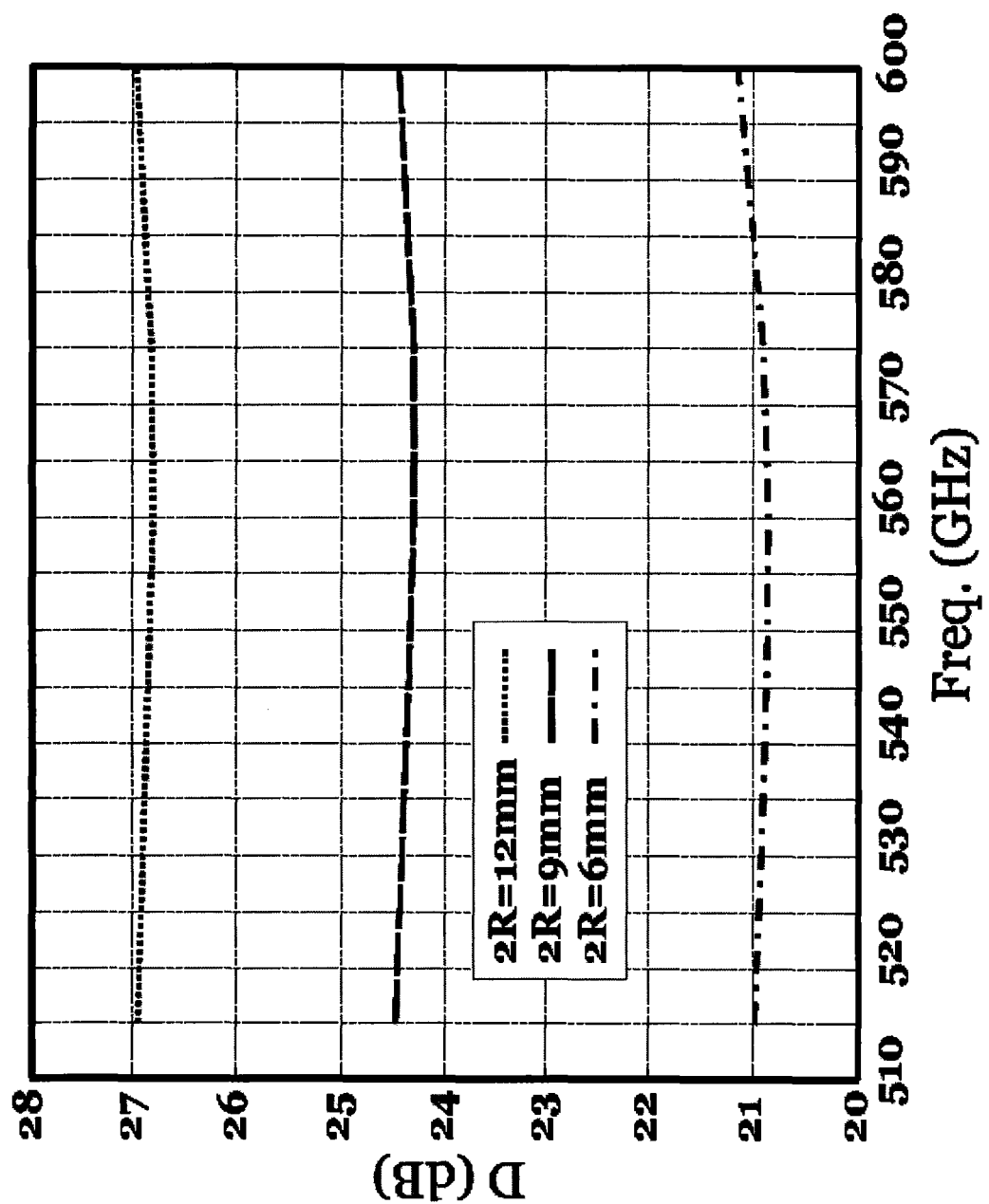
FIG. 10 shows directivity as a function of the central frequency (545 GHz) for several example lens diameters.
Figure 11:
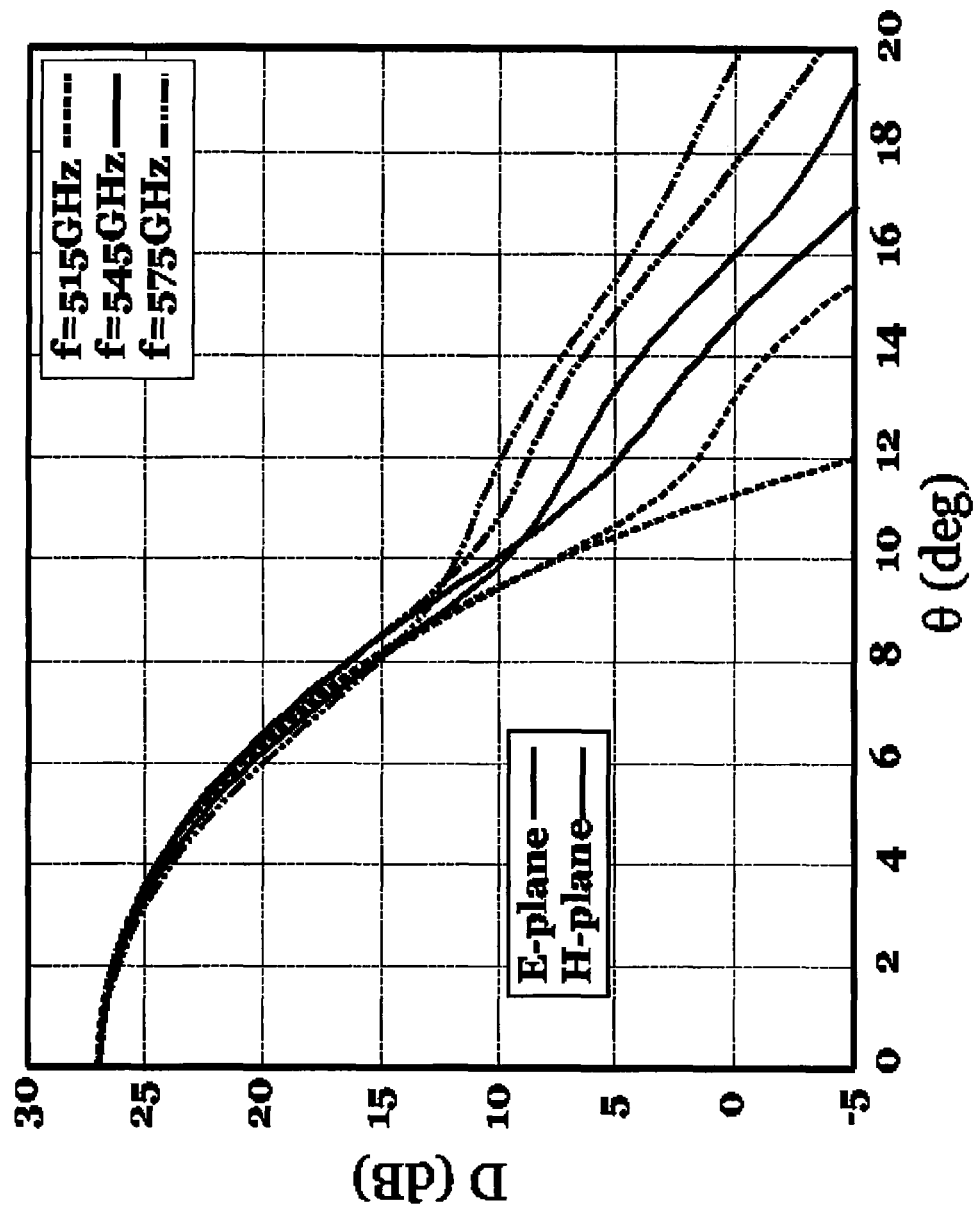
FIG. 11 shows example lens secondary patterns for several example frequencies and D=12 mm.

FIG. 10 shows the directivity as a function of the frequency for several example diameters at the optimum extension height calculated above. A linear behavior of the directivity might be expected since the diameter in terms of the wavelength is proportional to frequency. However, the directivities at the lower frequencies in FIG. 10 are slightly higher than at the central frequencies. This is because the primary feed is less directive at frequencies lower than the leaky wave resonant condition, which corresponds to a larger illuminated area. FIG. 11 shows the secondary patterns as a function of the frequency. The patterns present good rotational symmetry and low side-lobes for all the frequencies, and also exhibit gaussicity.

The standard extended hemispherical lens designs based on planar antennas suffer from very low tolerances of the feed positions. In Filippovic et al., "Off-Axis Properties of Silicon and Quartz Dielectric Lens Antennas", IEEE Trans. Antennas and Propagation, Vol. 45, no. 5, pp. 760-766, May 1997, which is incorporated by reference herein, the maximum allowable value of feed displacement d, without a significant increase in loss or decrease in the Gaussicity was set to X/R=0.12-0.14 for a silicon lens in order to correspond to a low equivalent f-number. In focusing optical components, this number is defined as the ratio between the focal distance, i.e. F=R+Lt, and the aperture diameter, i.e. $D_a$ (see FIG. 1b). In standard designs, the diffraction-limited extension height is 0.39, which corresponds to an f-number of f°/D°$_a$=0.695. In this case, a beam displacement of d=101.5 μm in a lens of $D_a$=3.83 mm will tilt the secondary pattern by a beamwidth, i.e. Δθ=8.23°, at 545 GHz.

The leaky wave lens antenna has a much better tolerance to off-axis displacements due to the directive primary feed which translates into a larger f-number. The actual value of the f-number depends on the feed taper illumination, which depends on the near-field distance as explained previously. For the example 2R=12 mm lens antenna shown in FIG. 7, the maximum directivity corresponds to an equivalent aperture diameter of approximately $D_a$=3.83 mm and an extension of $L_r$=0.2. The equivalent f-number is $f/D_a \approx 1.88$ in this case. This means that in order to tilt the beam by $\Delta\theta$=8.23°, the feed displacement is approximately 2.7 times larger than in the standard case.

Figure 12:
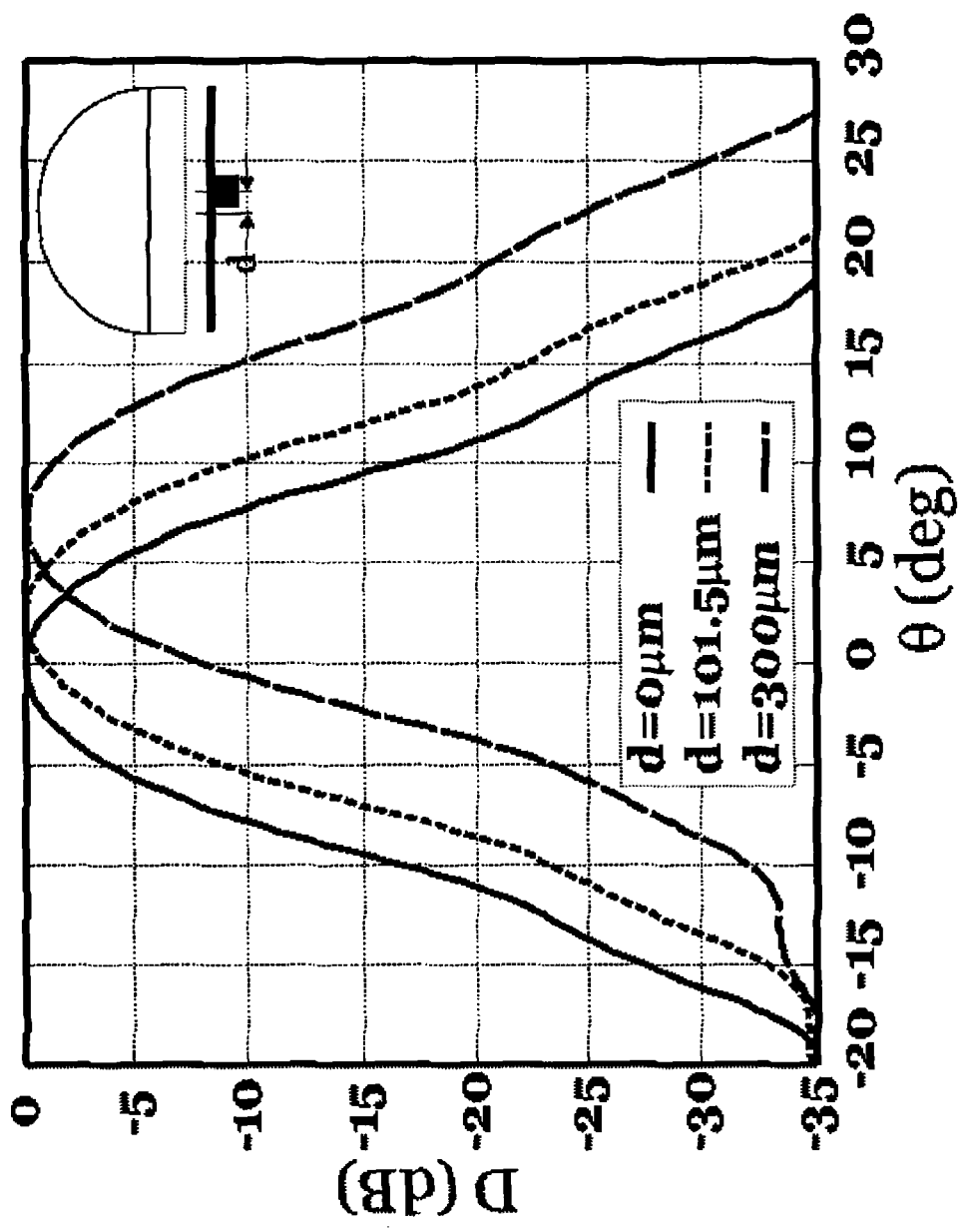
FIG. 12 shows example lens secondary patterns for off-axis beam displacements.
Figure 13A:
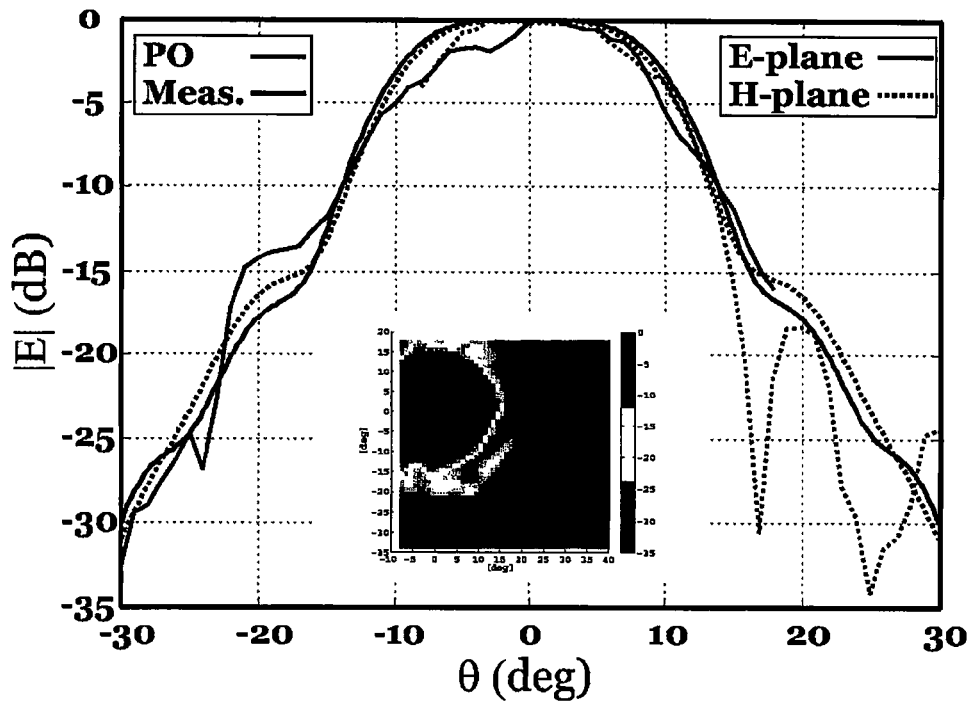
FIGS. 13A to 13D shows example measured radiation patterns at 545 GHz, 560 GHz, 575 GHz and 600 GHz, respectively.
Figure 13B:
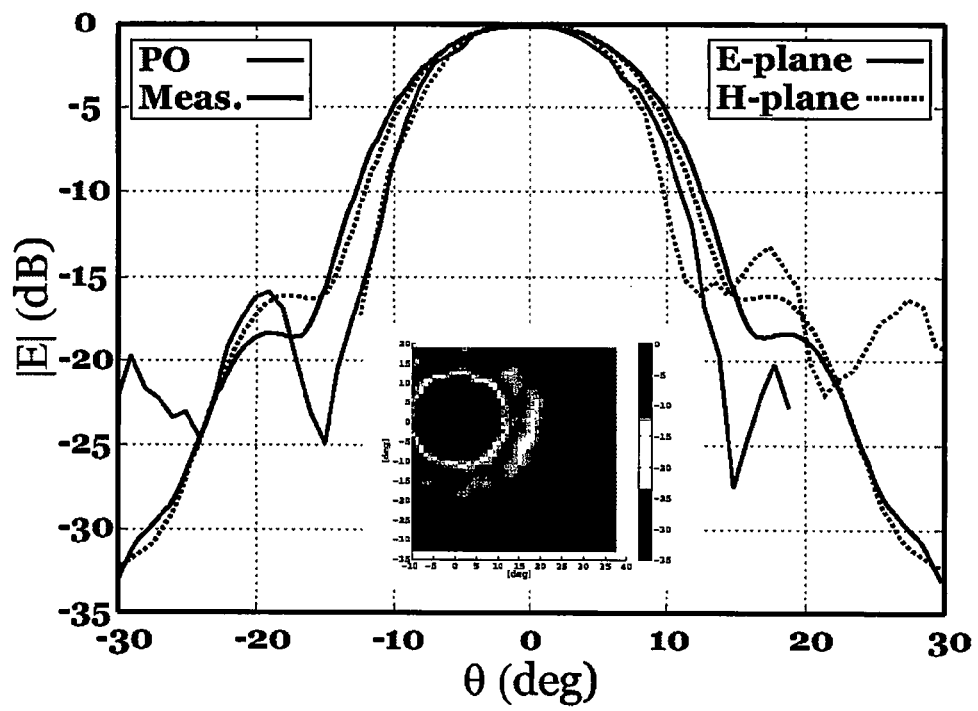
Figure 13C:
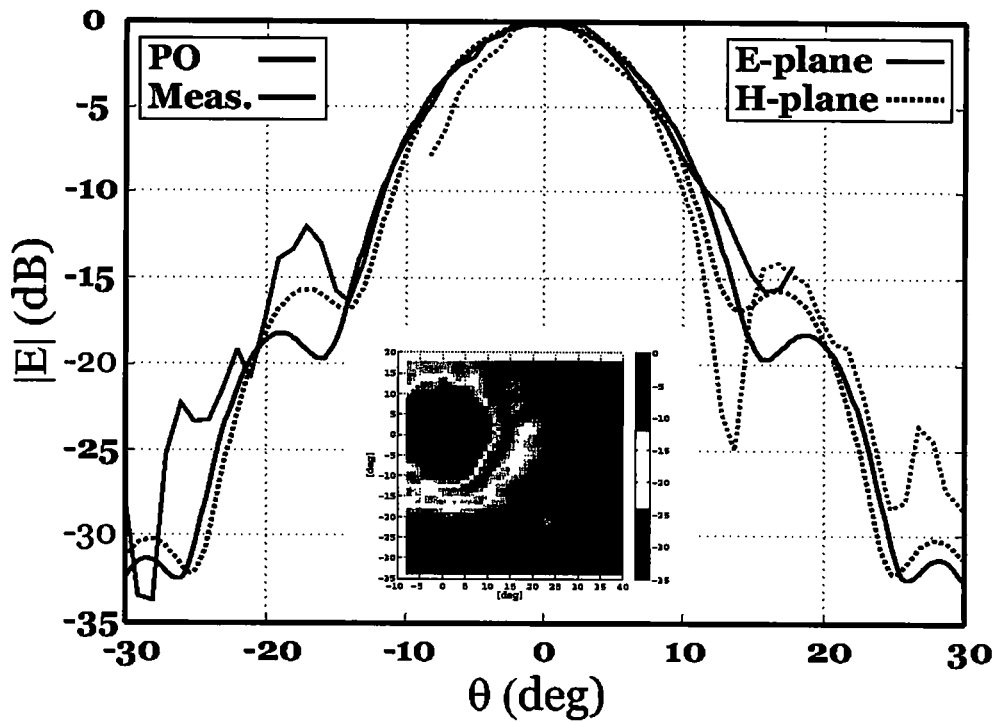
Figure 13D:
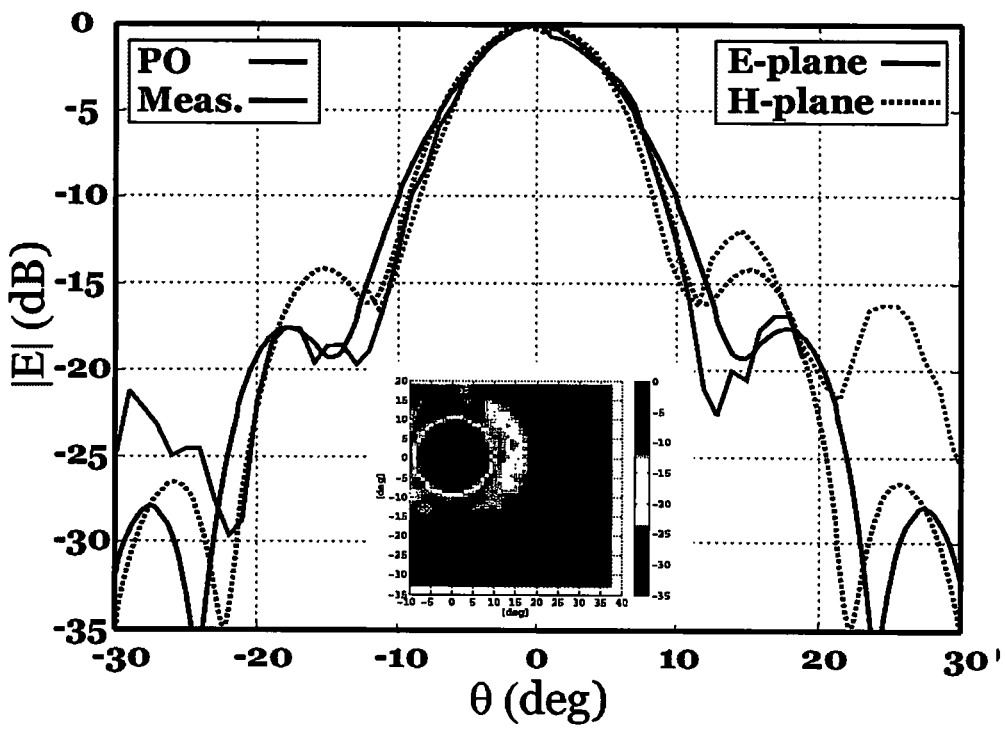

FIG. 12 shows the secondary patterns associated to the leaky wave feed with 2R=12 mm and $L_r$=0.2 for feed displacements of d=0 mm, 101.5 μm and d=300 μm. The beam is only scanned towards θ=2.35° for the same feed displacement that was scanning a whole beamwidth in the standard design, i.e. d=101.5 μm. Thus, the leaky wave lens antenna presents almost three times better tolerances to the feed position than standard double slot designs. Moreover, in analogy to reflector antennas, the off-focus feed distortions, if an array of primary feeds was to be used inside the lens, are lower for larger f-number systems.

3. Exemplary 545 GHz Integrated Lens

An example antenna in the 500-600 GHz band may be produced to prove functionality and evalutate the design. The example antenna may be built by assembling several parts fabricated separately prior to fabricating a complete antenna using photo-lithographic techniques. The waveguide, slot iris and air cavity (i.e. primary feed) may be fabricated in the same silicon wafer by using a three-step micro-machining process; whereas the micro-lens may be fabricated on a different wafer using photo-resist materials.

The assembled example antenna may include four basic pieces, a waveguide split block, a slot iris, an antenna cover and a silicon lens. The iris may be fabricated by etching the two slots from a 30 μm thick silicon wafer using a Bosch process Deep Reactive Ion Etching (DRIE). After the etching, the wafer may be sputtered with gold over the entire surface. The aluminum block includes the transition between a standard rectangular waveguide and a square waveguide, plus a 154 μm thick cut around the waveguide opening. This cut enables positioning of the iris and helps to provide the correct spacing between the iris and the lens, comprising the leaky wave cavity. An aluminum cover may be placed on top of the aluminum block with the silicon lens attached with cyanoacrylat. The central part of the cover may be approximately 150 μm thick. This cover both holds the iris in place and provides electrical contact between the iris and the waveguide block. In order to ensure the electric contact, a thin indium sheet may be employed in between these two components. The silicon lens may have the following dimensions: R=6 mm and L=−0.2857R, which are significantly different from the ideal height reported in FIG. 7, however it is adequate to validate the measured and simulated secondary patterns over the whole bandwidth.

The far fields of the prototype antenna have been measured using an ABmm network analyzer (see AB Millimetre, Paris http://www.abmillimetre.com/) and two rotating stages. The stages may be used to perform an azimuth and elevation far field scan. The scanning range may be limited to approximately 50° in both planes.

FIGS. 13A to 13D shows the main cuts of the measured patterns compared to the ones obtained with the PO method at 545 GHz, 560 GHz, 575 GHz and 600 GHz, respectively. Very good agreement is exhibited in the plots, considering that the noise floor of the measurement setup is around −30 dB and limited absorbing material was used to dump possible multiple reflections. The insets of these plots show the 2D measurements of the pattern amplitudes. During the measurements, the possible losses of the antenna may be assessed by computing the power budget of the system at 545 GHz. The transmission between two horns may be used as a reference. At 545 GHz, a difference of $P_d$=8 dB was measured in the received power between the two example setups, one with the lens antenna and the other with a horn antenna. In the power budget, the different directivities of the receiving antennas as well as additional losses in the receiver chain should be taken into account. In the example, directivity of the reference horn was higher than the lens antenna by approximately $D_d$=3 dB. The silicon lens antenna was connected to a network analyzer through a filter and two waveguide transitions, whereas the horn has the filter transition implemented in the same block. The loss of these components can be approximated by standard waveguide loss formulas to be $L_t$=3.5 dB. This implies that the actual loss of the lens antenna is in the order of approximately 1.5 dB.

4. Method of Producing a Planar Dielectric Antenna

Figure 14:
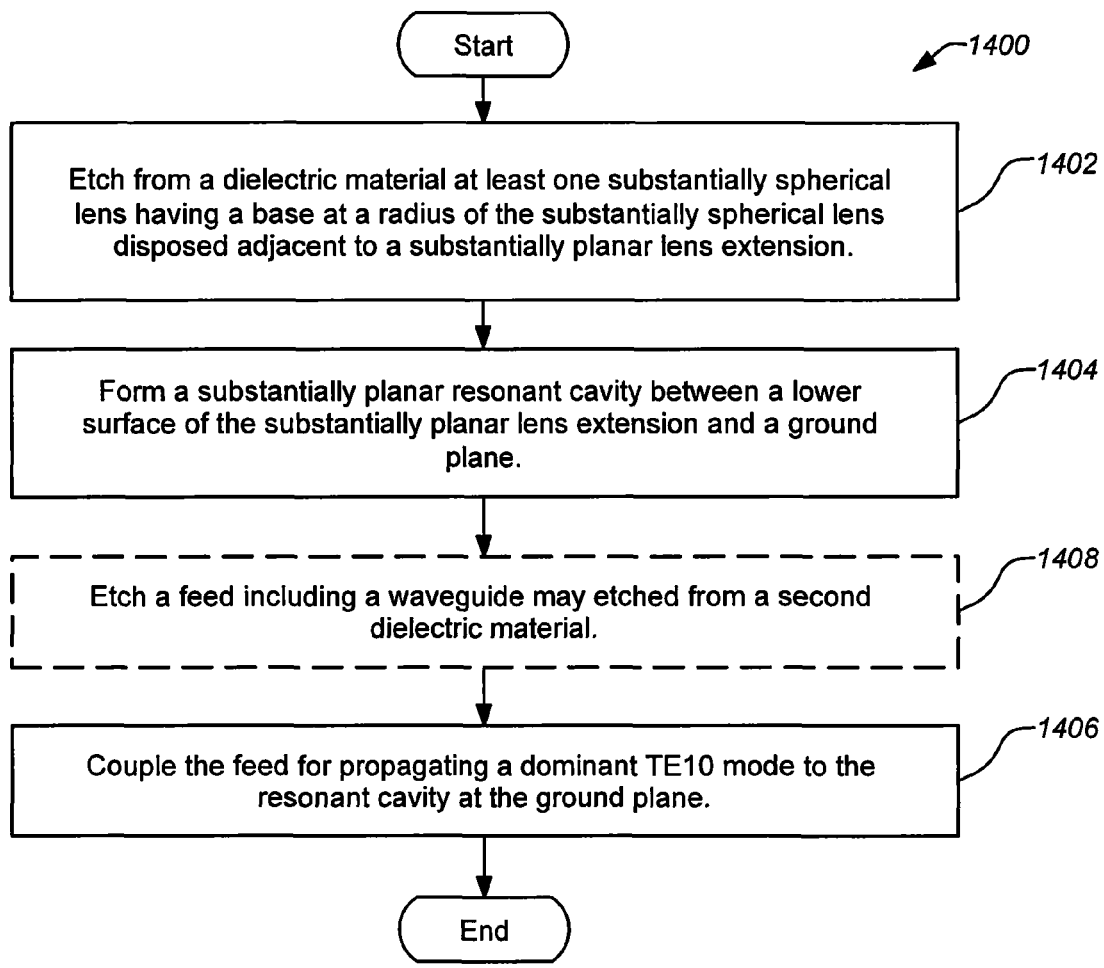
FIG. 14 is a flowchart of an exemplary method of producing a dielectric.

FIG. 14 is a flowchart of an exemplary method of producing a planar dielectric antenna. The method 1400 begins with an operation 1402 of etching from a dielectric material at least one substantially spherical lens having a base at a radius of the substantially spherical lens disposed adjacent to a substantially planar lens extension. In operation 1404 a substantially planar resonant cavity is formed between a lower surface of the substantially planar lens extension and a ground plane. Finally, in operation 1406 a feed for propagating a dominant $TE_{10}$ mode is coupled to the resonant cavity at the ground plane. In optional operation 1408, the feed including a waveguide may etched from a second dielectric material (which may be the same as the lens dielectric material) prior to coupling to the ground plane. The method 1400 may be further modified consistent with the apparatus embodiments previously described.

As previously discussed, one primary advantage of this antenna structure applied to the terahertz band is related to the fabrication. Since only a small sector of the lens is required (e.g. approximately 15°), the lens may be easy to microfabricate. This can enable the fabrication of an entire array of lenses on a common wafer. Thus, the array of primary feeds, e.g. including waveguide, slot iris and air cavity, may be fabricated in a single silicon wafer by using a three-step etching process. In addition, because the upper part of the lens presents only a small curvature and because the antenna with the lens may be fabricated photolithographically. This makes it possible to fabricate an array of lens antennas integrated on a single wafer. Moreover, the fabrication of the lens primary feed is compatible with silicon micro-machining techniques. See e.g., Chattopadhyay et al., "Deep Reactive Ion Etching based silicon micromachined components at terahertz frequencies for space applications", 33rd International Conference on Infrared, Millimeter and Terahertz Waves, 2008, 15-19 Sep. 2008, which is incorporated by reference herein. Thus, an array of microlenses and feeds may be fabricated on separate silicon wafers such that the assembly of an antenna array may be achieved by simply stacking and aligning two wafers.

This concludes the description including the preferred embodiments of the present invention. The foregoing description including the preferred embodiment of the invention has been presented for the purposes of illustration and description. It is not intended to be exhaustive or to limit the invention to the precise forms disclosed. Many modifications and variations are possible within the scope of the foregoing teachings. Additional variations of the present invention may be devised without departing from the inventive concept as set forth in the following claims.

What is claimed is:

1. An apparatus, comprising:
an extended spherical lens including a substantially spherical lens having a base at a radius of the substantially spherical lens disposed directly adjacent to a substantially planar lens extension; and a substantially planar resonant cavity defined between a ground plane and a lower surface of the substantially planar lens extension;

wherein a feed for propagating a dominant $TE_{10}$ mode is coupled to the resonant cavity at the ground plane and the substantially spherical lens and the substantially planar lens extension each comprise a dielectric material and the feed is coupled to the resonant cavity by an iris through the ground plane, the iris substantially matching impedance to the dominant $TE_{10}$ mode.

2. The apparatus of claim 1, wherein the substantially spherical lens comprises a hemispherical lens and the base comprises a great circle of the hemispherical lens.

3. The apparatus of claim 1, wherein the cavity comprises a dielectric material having a dielectric constant less than that of the substantially spherical lens and that of the substantially planar lens extension.

4. The apparatus of claim 1, wherein the substantially spherical lens comprises silicon.

5. The apparatus of claim 1, wherein the substantially spherical lens and the substantially planar lens extension are contiguous and produced from a common dielectric material.

6. The apparatus of claim 1, wherein the iris comprises a double arc slot through the ground plane.

7. The apparatus of claim 1, wherein the feed is coupled to the resonant cavity at the ground plane along a normal axis through the substantially spherical lens.

8. The apparatus of claim 1, wherein the feed is coupled to the resonant cavity at the ground plane substantially off a normal axis through the substantially spherical lens.

9. A method, comprising the steps of:
etching from a dielectric material at least one extended spherical lens each including a substantially spherical lens having a base at a radius of the substantially spherical lens disposed directly adjacent to a substantially planar lens extension;

forming a substantially planar resonant cavity between a lower surface of the substantially planar lens extension and a ground plane; and coupling a feed for propagating a dominant $TE_{10}$ mode to the resonant cavity at the ground plane;

wherein the substantially spherical lens and the substantially planar lens extension each comprise a dielectric material and the feed is coupled to the resonant cavity by an iris through the ground plane, the iris substantially matching impedance to the dominant $TE_{10}$ mode.

10. The method of claim 9, wherein the substantially spherical lens comprises a hemispherical lens and the base comprises a great circle of the hemispherical lens.

11. The method of claim 9, wherein the cavity comprises a dielectric material having a dielectric constant less than that of the substantially spherical lens and that of the substantially planar lens extension.

12. The method of claim 9, wherein the substantially spherical lens comprises silicon.

13. The method of claim 9, wherein the substantially spherical lens and the substantially planar lens extension are contiguous and produced from a common dielectric material.

14. The method of claim 9, wherein the iris comprises a double arc slot through the ground plane.

15. The method of claim 9, wherein the feed is coupled to the resonant cavity at the ground plane along a normal axis through the substantially spherical lens.

16. The method of claim 9, wherein the feed is coupled to the resonant cavity at the ground plane substantially off a normal axis through the substantially spherical lens.

17. An apparatus, comprising:
an array of extended spherical lenses each including a substantially spherical lens having a base at a radius of the substantially spherical lens and disposed directly adjacent to a substantially planar lens extension; and a substantially planar resonant cavity defined between a ground plane and a lower surface of the substantially planar lens extension;

wherein a feed for each of the extended spherical lenses for propagating a dominant $TE_{10}$ mode is coupled to the resonant cavity at the ground plane and the substantially spherical lens and the substantially planar lens extension each comprise a dielectric material and the feed is coupled to the resonant cavity by an iris through the ground plane, the iris substantially matching impedance to the dominant $TE_{10}$ mode.

18. The apparatus of claim 17, wherein the substantially planar lens extension comprises silicon.

19. The apparatus of claim 18, wherein the substantially planar lens extension comprises silicon from a common wafer with the substantially spherical lenses.

* * * * *